United States Patent
Lee et al.

(10) Patent No.: US 11,185,739 B2
(45) Date of Patent: Nov. 30, 2021

(54) ELECTRONIC DEVICE, AND METHOD FOR PROVIDING PERSONALISED EXERCISE GUIDE THEREFOR

(71) Applicant: Samsung Electronics Co., Ltd., Gyeonggi-do (KR)

(72) Inventors: Jungkun Lee, Seoul (KR); Dahee Lee, Incheon (KR); Jieun Lee, Seoul (KR); Yeseul Hong, Seoul (KR); Kwangwon Ko, Seoul (KR); Yeongsook Chae, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 351 days.

(21) Appl. No.: 16/064,159

(22) PCT Filed: Dec. 26, 2016

(86) PCT No.: PCT/KR2016/015259
§ 371 (c)(1),
(2) Date: Jun. 20, 2018

(87) PCT Pub. No.: WO2017/111564
PCT Pub. Date: Jun. 29, 2017

(65) Prior Publication Data
US 2019/0009136 A1    Jan. 10, 2019

(30) Foreign Application Priority Data

Dec. 24, 2015 (KR) .................. 10-2015-0186352

(51) Int. Cl.
*G16H 50/30* (2018.01)
*A63B 24/00* (2006.01)
(Continued)

(52) U.S. Cl.
CPC ........ *A63B 24/0075* (2013.01); *A61B 5/0205* (2013.01); *A63B 24/00* (2013.01);
(Continued)

(58) Field of Classification Search
None
See application file for complete search history.

(56) References Cited

U.S. PATENT DOCUMENTS 8,795,138 B1    8/2014  Yeh et al.
2007/0049461 A1  3/2007  Kim et al.
(Continued)

FOREIGN PATENT DOCUMENTS

CN    101151073 A    3/2008
CN    101518442 A    9/2009
(Continued)

OTHER PUBLICATIONS

European Search Report dated Nov. 12, 2018.
Chinese Search Report dated Sep. 2, 2019.

*Primary Examiner* — Bruk A Gebremichael
(74) *Attorney, Agent, or Firm* — Cha & Reiter, LLC

(57) ABSTRACT

A system for providing a personalised exercise guide according to various embodiments of the present invention may comprise: a wearable device for measuring a first bio-signal of a user using one or more sensors, and for transmitting to an electronic device and measured first bio-signal of the user; and the electronic device for receiving from the wearable device the measured first bio-signal of the user, for obtaining body data of the user based on the received first bio-signal of the user, for calculating a required quantity of exercise based on the obtained body data of the user and a preset goal, and for comparing and analyzing body data variation of the user that is estimated based on the (Continued)

calculated required quantity of exercise with the actual body data variation of the user due to exercise.

13 Claims, 15 Drawing Sheets

(51) Int. Cl.
  *G16H 20/30* (2018.01)
  *G16H 40/63* (2018.01)
  *A61B 5/0205* (2006.01)
  *A61B 5/389* (2021.01)
  *A61B 5/0245* (2006.01)
  *A61B 5/08* (2006.01)
  *A61B 5/107* (2006.01)
  *A61B 5/11* (2006.01)
  *A61B 5/16* (2006.01)
  *A61B 5/22* (2006.01)

(52) U.S. Cl.
  CPC ............ *G16H 20/30* (2018.01); *G16H 40/63* (2018.01); *G16H 50/30* (2018.01); *A61B 5/0245* (2013.01); *A61B 5/0816* (2013.01); *A61B 5/107* (2013.01); *A61B 5/112* (2013.01); *A61B 5/165* (2013.01); *A61B 5/224* (2013.01); *A61B 5/389* (2021.01); *A63B 2024/0065* (2013.01); *A63B 2024/0068* (2013.01); *A63B 2230/01* (2013.01); *A63B 2230/06* (2013.01); *A63B 2230/42* (2013.01); *A63B 2230/62* (2013.01); *A63B 2230/70* (2013.01)

(56) References Cited

U.S. PATENT DOCUMENTS

| 2008/0096726 | A1* | 4/2008 | Riley ................ A63B 24/0006 482/8 |
| 2009/0024233 | A1 | 1/2009 | Shirai et al. |
| 2013/0274635 | A1 | 10/2013 | Coza et al. |
| 2015/0037771 | A1* | 2/2015 | Kaleal, III ........... A61B 5/0022 434/257 |
| 2015/0359480 | A1 | 12/2015 | Guthrie et al. |

FOREIGN PATENT DOCUMENTS

| CN | 103372298 A | 10/2013 |
| KR | 10-0714093 B1 | 5/2007 |
| KR | 10-2009-0089735 A | 8/2009 |
| KR | 10-2014-0015678 A | 2/2014 |
| KR | 10-2014-0133685 A | 11/2014 |
| KR | 10-2015-0032182 A | 3/2015 |
| KR | 10-2015-0107268 A | 9/2015 |

* cited by examiner

FIG. 6B
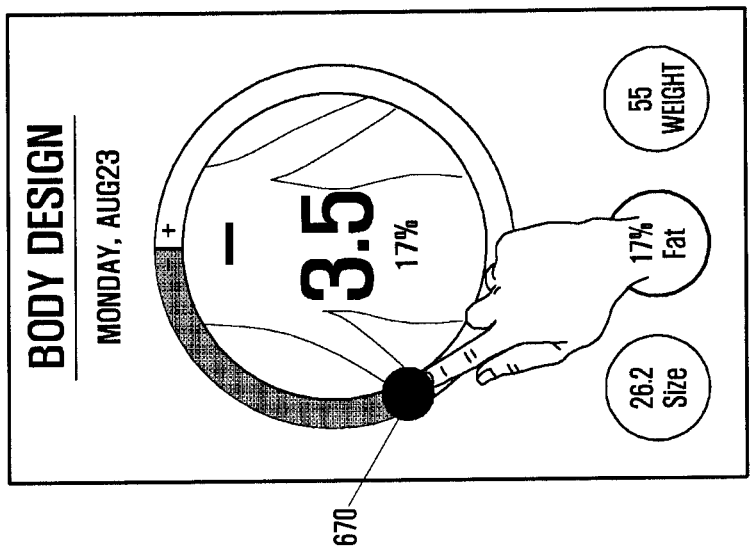
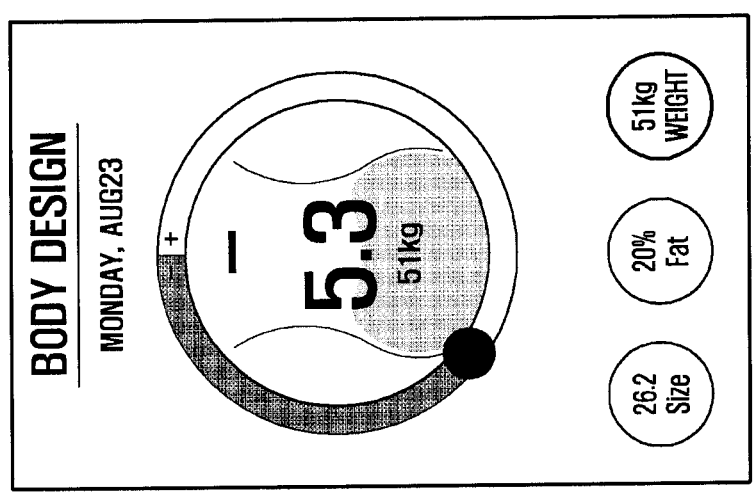
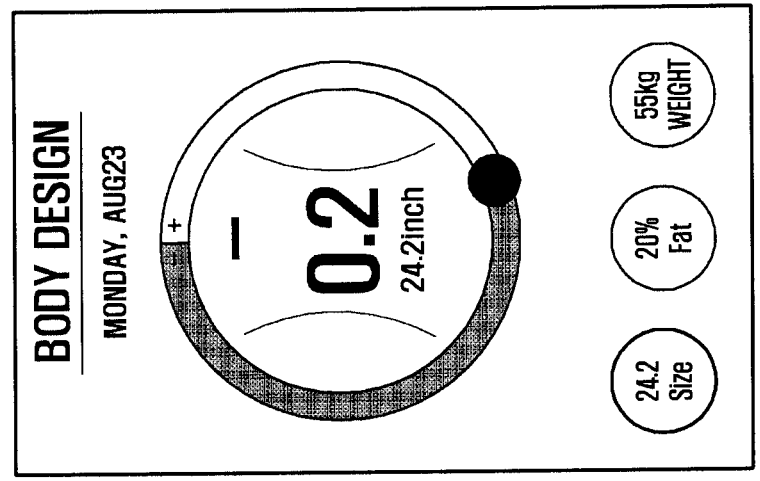

ELECTRONIC DEVICE, AND METHOD FOR PROVIDING PERSONALISED EXERCISE GUIDE THEREFOR

CLAIM OF PRIORITY

This application is a National Phase Entry of PCT International Application No. PCT/KR2016/015259, which was filed on Dec. 26, 2016 and claims a priority to Korean Patent Application No. 10-2015-0186352, which was filed on Dec. 24, 2015, the contents of which are incorporated herein by reference.

TECHNICAL FIELD

The present invention relates to an electronic device, method, and system for providing a personalized exercise guide. More particularly, the present invention relates to a method for providing a personalized exercise guide through an electronic device using a wearable device.

BACKGROUND ART

As people's interest in healthcare and fitness has increased in recent years, a variety of devices are developed for more scientific management of workout and health, especially fatness management. For example, simple wearable devices are introduced to measure the amount of workout.

For example, there are some devices that measure the amount of workout by measuring a heart rate highly correlated with calorie consumption during aerobic exercise. As one example, the user can wear a chest belt on his or her chest to measure a heart rate. As another example, the user may use as an arm band type device capable of measuring a heart rate through an optical sensor at a user's inner forearm or use other device capable of measuring a heart rate through a ring type optical sensor on a user's finger.

DISCLOSURE OF INVENTION

Technical Problem

The present invention is to provide a customized or personalized exercise guide to a user who uses a device for measuring the amount of workout.

Solution to Problem

According to various embodiments of the present invention, a method for providing a personalized exercise guide at an electronic device may comprise receiving a user's first biometric signal measured by at least one sensor; acquiring user's body data, based on the received first biometric signal; calculating a required amount of workout, based on the acquired body data and a pre-established goal; and comparing and analyzing a body data change estimated based on the calculated required amount of workout and an actual body data change resulting from workout.

According to various embodiments of the present invention, an electronic device may comprise a communication module receiving a user's first biometric signal measured by at least one sensor included in another electronic device; a display displaying body data and a required amount of workout; a memory storing instructions; and a processor electronically connected to the communication module, the display, and the memory, wherein the instructions stored in the memory cause, upon execution, the processor to acquire user's body data, based on the received first biometric signal, to calculate a required amount of workout, based on the acquired body data and a pre-established goal, and to compare and analyze a body data change estimated based on the calculated required amount of workout and an actual body data change resulting from workout.

According to various embodiments of the present invention, a system for providing a personalized exercise guide may comprise a wearable device measuring a user's first biometric signal through at least one sensor, and transmitting the measured first biometric signal to an electronic device; and the electronic device receiving the measured first biometric signal from the wearable device, acquiring user's body data, based on the received first biometric signal, calculating a required amount of workout, based on the acquired body data and a pre-established goal, and comparing and analyzing a body data change estimated based on the calculated required amount of workout and an actual body data change resulting from workout.

Advantageous Effects of Invention

Various embodiments of the present invention may provide a personalized exercise guide to a user of an electronic device and/or a wearable device.

BRIEF DESCRIPTION OF DRAWINGS

FIGS. 6A to 7 are exemplary diagrams showing a user interface allowing a user to establish a goal in an embodiment.

MODE FOR THE INVENTION

Figure 1:
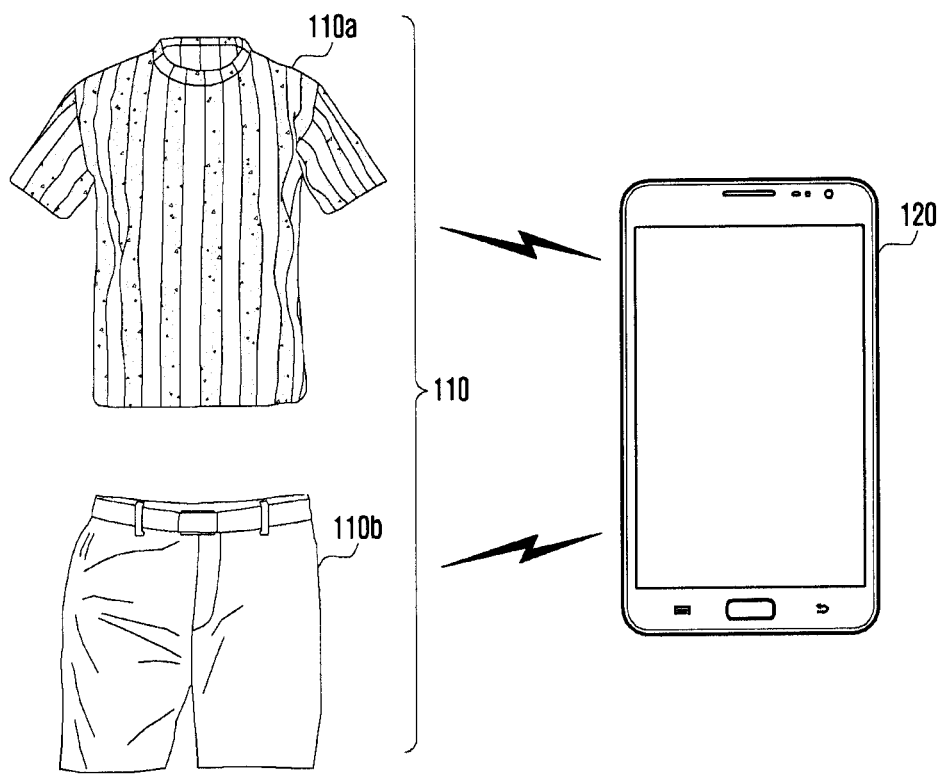
FIG. 1 illustrates an environment of a system for providing a personalized exercise guide according to various embodiments.

Hereinafter, various embodiments of the present disclosure are described with reference to the accompanying drawings. It should be understood that embodiments and terminology used therein are not intended to limit the disclosed technique to particular implementation, but various modifications, equivalents, and/or alternatives of the embodiments are included. In the description of the drawings, like reference numerals may be used for similar elements. The singular expressions may include plural expressions unless the context clearly dictates otherwise. In this disclosure, the expressions "A or B", "at least one of A and/or B", and the like may include all possible combinations of items listed together. The expressions including ordinal numbers, such as "first" and "second," may indicate various elements regardless of the sequence or importance of the elements, and are used merely for the purpose to distinguish one element from the others. When a certain element (e.g., first element) is referred to as being "connected" or "coupled" (operatively or communicatively) to another element (e.g., second element), it may mean that the first element is connected or coupled directly to the second element or indirectly through any other element (e.g., third element).

The expression "configured to" may be interchangeably used with any other expressions "suitable for", "having the ability to", "designed to", "adapted to", "made to", "being able to", and "capable of". The expression "device configured to" may mean that the device, together with other devices or components, "is able to". For example, the phrase "processor configured to perform A, B and C" may mean a dedicated processor (e.g., embedded processor) for performing corresponding operations or a generic-purpose processor (e.g., central processing unit (CPU) or application processor (AP)) capable of performing corresponding operations by executing one or more software programs stored in a memory.

An electronic device according to various embodiments of this disclosure may include at least one of a smart phone, a tablet personal computer (PC), a mobile phone, a video phone, an e-book reader, a desktop PC, a laptop PC, a netbook computer, a workstation, a server, a personal digital assistant (PDA), a portable multimedia player (PMP), an MP3 player, a portable medical device, a digital camera, or a wearable device. According to various embodiments, the wearable device may include at least one of an accessory-type device (e.g., a watch, a ring, a bracelet, an anklet, a necklace, glasses, a contact lens, or a head-mounted device (HMD), a fabric- or cloth-type device (e.g., electronic cloth), a body-attached type device (e.g., a skin pad or tattoo), or a body-implemented type circuit. In some embodiments, the electronic device may be home appliance. For example, the home appliance may include at least one of a TV, a digital video disk (DVD) player, audio equipment, a refrigerator, an air conditioner, a vacuum cleaner, an oven, a microwave, a washing machine, an air cleaner, a set-top box, a home automation control panel, a security control panel, a media box (e.g., Samsung HomeSync™, Apple TV™, or Google TV™), a game console (e.g., Xbox™, PlayStation™), an electronic dictionary, an electronic key, a camcorder, or an electronic picture frame.

In another embodiment, the electronic device may include at least one of a medical device (e.g., portable medical measuring equipment (e.g., a blood sugar meter, a heart rate meter, a blood pressure meter, a clinical thermometer, etc.), a magnetic resonance angiography (MRA), a magnetic resonance imaging (MRI), a computed tomography (CT), an ultrasonography, etc.), a navigation device, a global navigation satellite system (GNSS), an event data recorder (EDR), a flight data recorder (FDR), a car infotainment device, electronic equipment for ship (e.g., a marine navigation system, a gyrocompass, etc.), avionics, security equipment, a car head unit, an industrial or home robot, a drone, an automated teller machine (ATM), a point of sales (POS), or a device for internet of things (IoT) (e.g., a bulb, a sensor, a sprinkler, a fire alarm, a thermostat, a streetlight, a toaster, athletic equipment, a hot-water tank, a heater, a boiler, etc.). In a certain embodiment, the electronic device may be include at least one of furniture, a part of a building/construction or car, an electronic board, an electronic signature receiving device, a projector, or various measuring instruments (e.g., a water meter, an electric meter, a gas meter, a wave meter, etc.). In various embodiments, the electronic device may be one of the above-mentioned devices or a combination thereof. The electronic device according to embodiments disclosed herein is not limited to the above-mentioned devices and may include new electronic devices to be launched with the growth of technology. In this disclosure, the term user may refer to a person or a device (e.g., an artificial intelligence device) using an electronic device.

FIG. 1 illustrates an environment of a system for providing a personalized exercise guide according to various embodiments.

According to various embodiments, a wearable device 110 or an electronic device 120 may measure a biometric signal of a user who wears the wearable device 110. The wearable device 110 may include at least one of an accessory-type device (e.g., a watch, a ring, a bracelet, an anklet, a necklace, glasses, a contact lens, or a head-mounted device (HMD), a fabric- or cloth-type device (e.g., electronic cloth), a body-attached type device (e.g., a skin pad or tattoo), or a body-implemented type circuit. For example, in case of a fabric- or cloth-type device, the wearable device 110 may be integrated with or embedded in shirt, pants, underwear, or the like. In some embodiments, the wearable device 110 may be in the form of at least one of socks, gloves, shoes, a belt, a band, and a ring.

The biometric signal measured by the wearable device 110 may be, for example, heartbeat, electrocardiogram (ECG), respiration, body fat, acceleration, size, electromyogram (EMG), and the like. The wearable device 110 may include a sensor module such as an ECG sensor, an acceleration sensor, an EMG sensor, a respiratory sensor, and a body fat sensor. In some embodiments, the wearable device 110 may omit at least one of the above sensors or add any other sensor.

According to various embodiments, in case where the electronic device 120 needs to measure user's biometric data, the electronic device 120 may request at least part of related function or service from the wearable device 110 instead of or in addition to directly performing such a function or service. For example, the wearable device 110 may measure a biometric signal by using the sensor module and transmit the measured biometric signal to the electronic device 120 via a communication interface.

According to various embodiments, at least one wearable device 110 may transmit a user's biometric signal to the electronic device 120. If each of a plurality of wearable devices (e.g., 110a and 110b) transmits a user's biometric signal to the electronic device 120, the respective wearable devices 110a and 110b may transmit the biometric signals to the electronic device 120 in different cycles to avoid overlap of signals.

According to various embodiments of the present invention, a system for providing a personalized exercise guide may comprise a wearable device measuring a user's first biometric signal through at least one sensor, and transmitting the measured first biometric signal to an electronic device; and the electronic device receiving the measured first biometric signal from the wearable device, acquiring user's body data, based on the received first biometric signal, calculating a required amount of workout, based on the acquired body data and a pre-established goal, and comparing and analyzing a body data change estimated based on the calculated required amount of workout and an actual body data change resulting from workout.

Figure 2:
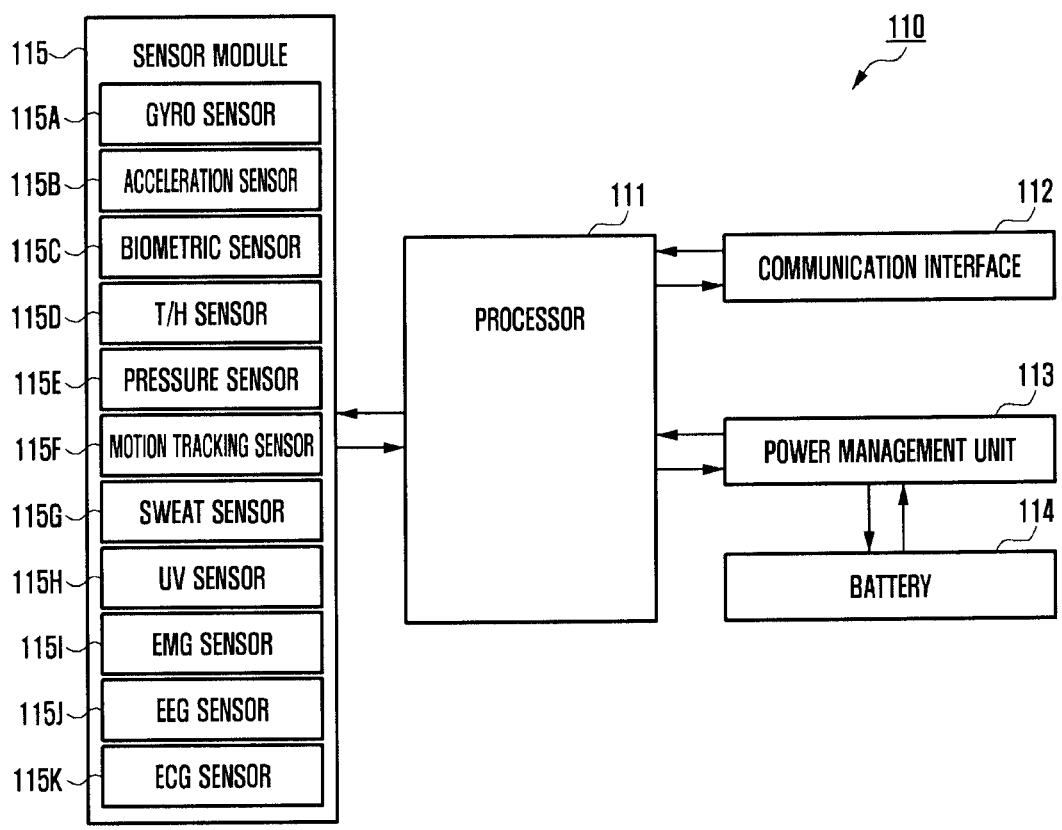
FIG. 2 is a block diagram of a wearable device according to various embodiments.

FIG. 2 is a block diagram of a wearable device 110 according to various embodiments.

According to various embodiments, the wearable device 110 may include one or more processors 111 (e.g., an AP), a communication interface 112, a power management unit 113, a battery 114, and a sensor module 115. In some embodiments, the wearable device 110 may omit at least one of the above elements or further include any other element.

The processor 111 may include at least one of a central processing unit (CPU), an application processor (AP), or a communication processor (CP). The processor 120 may perform an operation or data processing for control and/or communication of at least one of other elements.

The communication interface 112 may include, for example, wireless communication or wired communication. The wireless communication may include cellular communication using at least one of, for example, LTE, LTE Advance (LTE-A), code division multiple access (CDMA), wideband CDMA (WCDMA), universal mobile telecommunications system (UMTS), wireless broadband (WiBro), global system for mobile communications (GSM), and the like. According to an embodiment, the wireless communication may include at least one of, for example, wireless fidelity (WiFi), Bluetooth, Bluetooth low power (BLE), Zigbee, near field communication (NFC), magnetic secure transmission, radio frequency (RF), or body area network (BAN). According to an embodiment, the wireless communication may include GNSS. The GNSS may be, for example, global positioning system (GPS), global navigation satellite system (Glonass), Beidou navigation satellite system (Beidou), or Galileo, the European global satellite-based navigation system. Hereinafter, in this disclosure, "GPS" may be used interchangeably with "GNSS". The wired communication may include at least one of, for example, a universal serial bus (USB), a high definition multimedia interface (HDMI), a recommended standard 232 (RS-232), a power line communication, or a plain old telephone service (POTS).

The power management unit 113 may manage the power of the wearable device 110. According to an embodiment, the power management unit may include a power management integrated circuit (PMIC), a charger IC, or a battery or fuel gauge. The PMIC may be available for at least one of wired and wireless charging schemes. The wireless charging scheme may include, for example, a magnetic resonance scheme, a magnetic induction scheme, or an electromagnetic scheme. In addition, any additional circuit for wireless charging may be used such as a coil loop, a resonance circuit, or a rectifier. The battery gauge may measure the residual amount of battery, and a voltage, current or temperature in a charging process. A battery 114 may include, for example, a rechargeable battery and/or a solar battery.

The sensor module 115 may, for example, measure a biometric signal of a user wearing the wearable device 110 or detect an operating state of the wearable device 100, and then convert the measured or detected information into an electrical signal. The sensor module 115 may include, for example, at least one of a gyro sensor 115A, an acceleration sensor 115B, a biometric sensor 115C, a temperature/humidity sensor 115D, a pressure sensor 115E, a motion tracking sensor 115F, a sweat sensor 115G, a ultraviolet (UV) sensor 115H, an electromyography (EMG) sensor 115I, an electroencephalogram (EEG) sensor 115J, and an electrocardiogram (ECG) sensor 115K. The sensor module 115 may further include a control circuit for controlling one or more sensors included therein. In a certain embodiment, the wearable device 110 may further include a processor dedicated to the sensor module, either as part of or separately from the processor 111, to control the sensor module while the processor 111 is in a sleep state.

According to various embodiments, the above elements of the wearable device 110 may be configured to be removable. This is because, when the wearable device 110 has a form of garment, electrically coupled elements may be damaged during washing or the like. In a certain embodiment, the wearable device 110 may be waterproof coated to prevent such damage.

Figure 3:
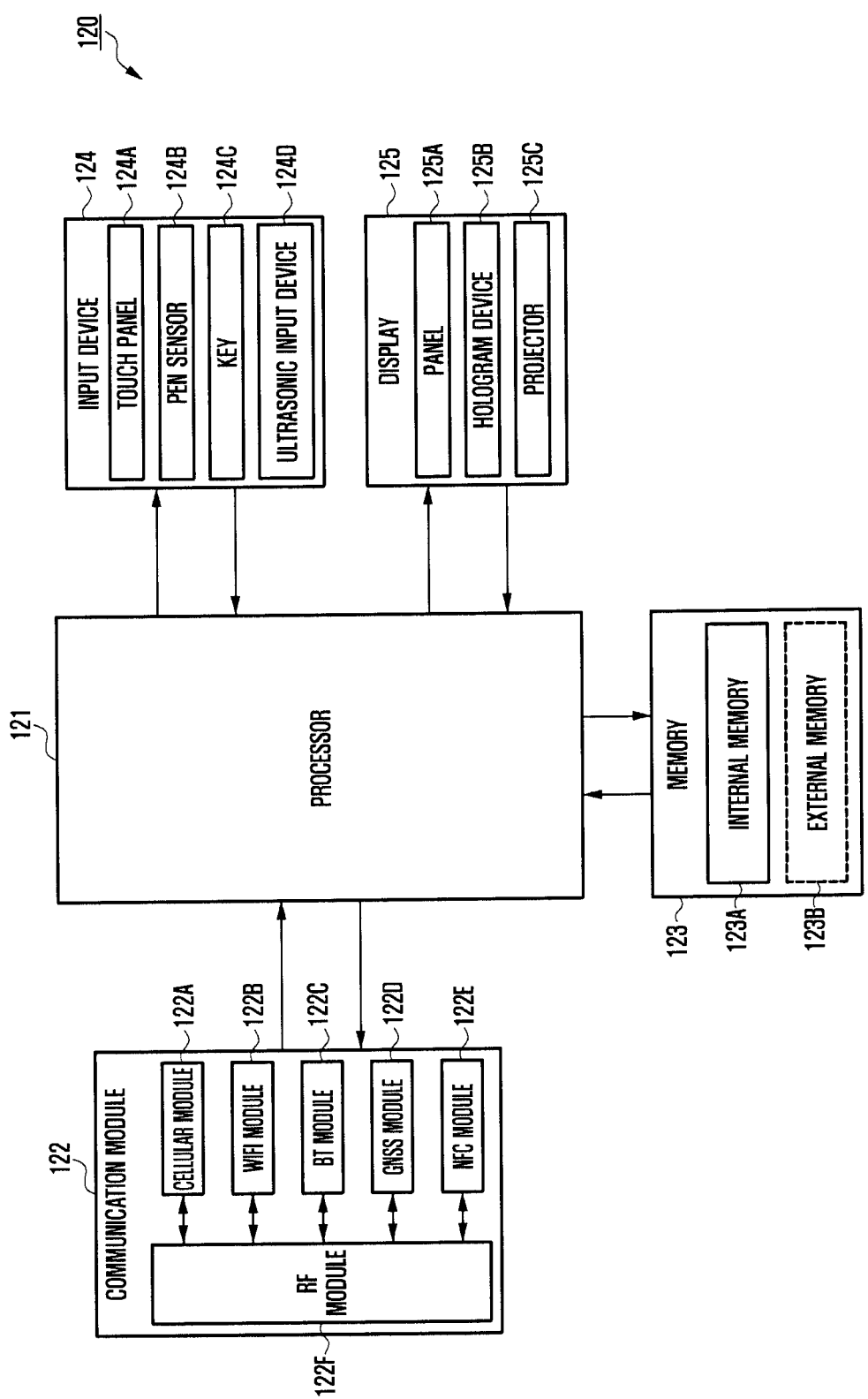
FIG. 3 is a block diagram of an electronic device according to various embodiments.

FIG. 3 is a block diagram of an electronic device 120 according to various embodiments.

According to various embodiments, the electronic device 120 may include one or more processors 121 (e.g., an AP), a communication module 122, a memory 123, an input device 124, and a display 125. In some embodiments, the electronic device 120 may omit at least one of the above elements or further include any other element.

The processor 121 may execute an operating system (OS) or an application program, control hardware or software components connected thereto, and perform processing and operations on various data. The processor 121 may be implemented by, for example, a system on chip (SoC). According to an embodiment, the processor 121 may further include a graphic processing unit (GPU) and/or an image signal processor. The processor 121 may load instructions or data received from at least one of the other elements (e.g., non-volatile memory) into volatile memory, process them, and then store the resulting data in non-volatile memory.

The communication module 122 may include, for example, a cellular module 122A, a WiFi module 122B, a Bluetooth module 122C, a GNSS module 122D, an NFC module 122E, and an RF module 122F. The cellular module 122A may provide a voice call, a video call, a messaging service, or an Internet service, for example, through a communication network. According to an embodiment, the cellular module 122A may utilize a subscriber identity module (e.g., a SIM card) to perform the identification and authentication of the electronic device 120 in the communication network. According to an embodiment, the cellular module 122A may perform at least some of functions that the processor can provide. According to an embodiment, the cellular module 122A may include a communications processor (CP). According to a certain embodiment, at least some (e.g., two or more) of the cellular module 122A, the WiFi module 122B, the Bluetooth module 122C, the GNSS module 122D, or the NFC module 122E may be included in a single integrated chip (IC) or IC package. The RF module 122F may, for example, transmit and receive communication signals (e.g., RF signals). The RF module 122F may include, for example, a transceiver, a power amplifier module (PAM), a frequency filter, a low noise amplifier (LNA), or an antenna. According to another embodiment, at least one of the cellular module 122A, the WiFi module 122B, the Bluetooth module 122C, the GNSS module 122D, and the NFC module 122E may transmit and receive RF signals through the RF module 122F.

The memory 123 may include, for example, an internal memory 123A or an external memory 123B. The internal memory 123A may include, for example, at least one of a volatile memory (e.g., a DRAM, an SRAM, or SDRAM), and a non-volatile memory (e.g., a one-time programmable ROM (OTPROM), a PROM, an EPROM, an EEPROM, a mask ROM, a flash ROM, a flash memory, a hard drive, or a solid state drive (SSD)). The external memory 123B may include a flash drive, for example, a compact flash (CF), a secure digital (SD), a micro-SD, a mini-SD, an extreme Digital (xD), or a memory stick. The external memory 123B may be functionally or physically connected to the electronic device 120 through various interfaces.

The input device 124 may include, for example, a touch panel 124A, a digital pen sensor 124B, a key 124C, or an ultrasonic input device 124D. The touch panel 124A may use at least one scheme of capacitive type, resistive type, infrared type, or ultrasonic type. Also, the touch panel 124A may further include a control circuit. The touch panel 124A may further include a tactile layer to offer a tactile feedback to a user. The digital pen sensor 124B may be a part of the touch panel 124A or include a separate recognition sheet. The key 124C may include, for example, a physical button, an optical key, or a keypad. The ultrasonic input device 124D may sense, through a microphone, ultrasonic waves generated at an input tool and identify data corresponding to the sensed ultrasonic waves.

The display 125 may include a panel 125A, a hologram device 125B, a projector 125C, and/or a control circuit for controlling them. The panel 125A may be implemented to be flexible, transparent, or wearable. The panel 125A may be formed of a single module with the touch panel. The hologram device 125B may show a stereoscopic image in the air by using interference of light. The projector 125C may project an image onto a screen, which may be located at the inside or outside of the electronic device 120.

Although FIGS. 2 and 3 separately show the wearable device 110 and the electronic device 120, the present invention is not limited thereto. The wearable device 110 and the electronic device 120 may be configured to operate by a single processor in a single device.

According to various embodiment of the present invention, an electronic device may comprise a communication module receiving a user's first biometric signal measured by at least one sensor included in another electronic device; a display displaying body data and a required amount of workout; a memory storing instructions; and a processor electronically connected to the communication module, the display, and the memory, wherein the instructions stored in the memory cause, upon execution, the processor to acquire user's body data, based on the received first biometric signal, to calculate a required amount of workout, based on the acquired body data and a pre-established goal, and to compare and analyze a body data change estimated based on the calculated required amount of workout and an actual body data change resulting from workout.

According to various embodiment of the present invention, the another electronic device may be a fabric-type or cloth-type wearable device.

According to various embodiment of the present invention, the electronic device may further comprise an input device receiving an input for establishing a goal.

According to various embodiment of the present invention, the instructions may further cause the processor to determine whether a result of comparing and analyzing the estimated body data change and the actual body data change is out of a predetermined error range, and to correct the calculated required amount of workout when the result is out of the predetermined error range.

According to various embodiment of the present invention, the instructions may further cause the processor to monitor a user's workout state.

According to various embodiment of the present invention, the instructions may further cause the processor
to detect a change in motions and biometric signals of the user, and to determine whether the user is in a state of workout, based on the detected change in motions and biometric signals.

According to various embodiment of the present invention, the instructions may further cause the processor to receive a user's second biometric signal measured by the at least one sensor, to collect a change in user's body data, based on the received second biometric signal, to identify a user's workout state, based on the collected change in body data, and to display a personalized exercise guide, based on the identified user's workout state.

According to various embodiment of the present invention, the instructions may further cause the processor to display a recommended workout analyzed based on the received first and second biometric signals.

Figure 4:
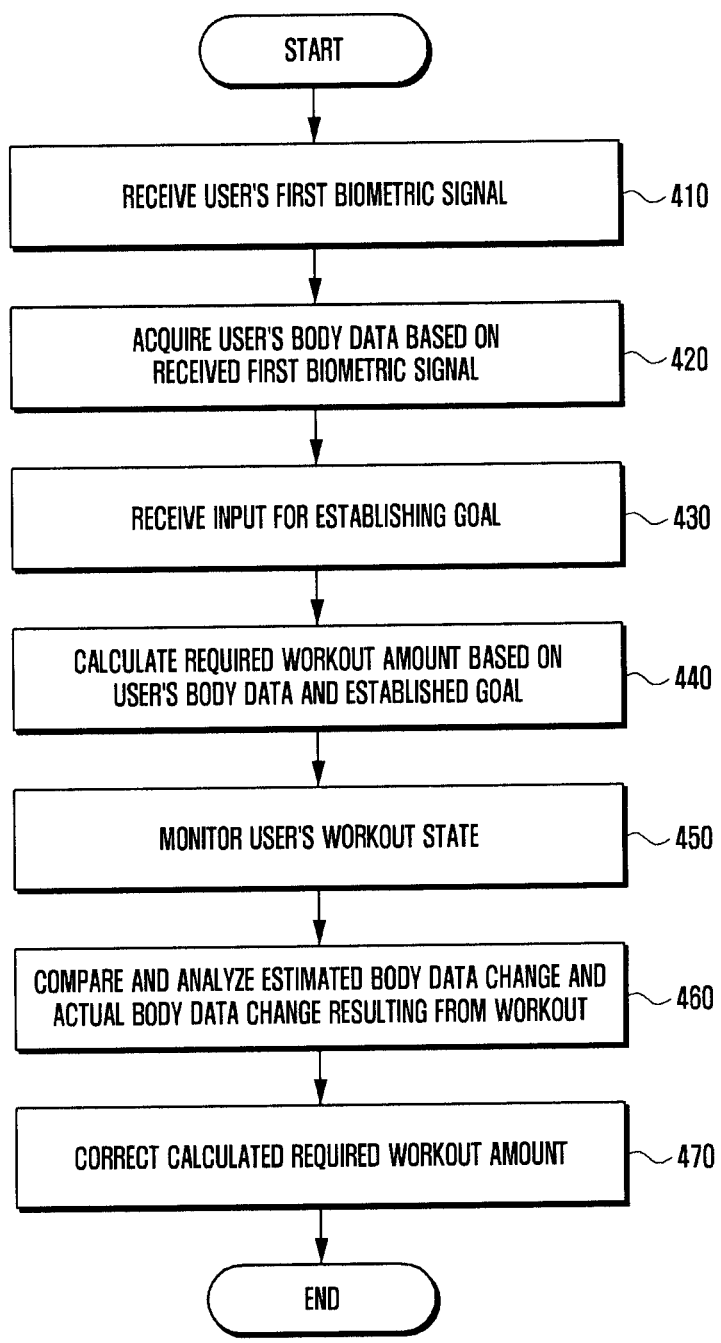
FIG. 4 is a flow diagram illustrating a method for personalizing and calculating a required workout amount according to various embodiments.

FIG. 4 is a flow diagram illustrating a method for calculating a personalized, required workout amount according to various embodiments.

Referring to FIG. 4, at operation 410, the electronic device 120 may receive a user's first biometric signal measured by a sensor.

According to various embodiments, the electronic device 120 may control the wearable device 110 to measure the first biometric signal of the user who wears the wearable device 110. For example, when an input for measuring the user's first biometric signal is received, the electronic device 120 may transmit a command to measure the user's first biometric signal to the wearable device 110 via the communication module 122. The wearable device 110 that receives the command may control the sensor module 115 to measure the first biometric signal of the user wearing the wearable device 110. When the user's first biometric signal is measured, the wearable device 110 may transmit the measured first biometric signal to the electronic device 120 via the communication interface 112. Then, the electronic device 120 may receive the user's first biometric signal through the communication module 122.

According to various embodiments, the sensor module 115 may include at least one of the gyro sensor 115A, the acceleration sensor 115B, the biometric sensor 115C, the temperature/humidity sensor 115D, the pressure sensor 115E, the motion tracking sensor 115F, the sweat sensor 115G, the UV sensor 115H, the EMG sensor 115I, the EEG sensor 115J, and the ECG sensor 115K.

The user's biometric signal measured by the sensor module 115 may include at least one of heart rate, blood pressure, blood oxygen saturation, heart rhythm, respiration rate, electromyogram, blood glucose, body temperature, body fat, stress, body size, and workout acceleration. For example, the user's heart rate measured by the ECG sensor 115K may be used to determine at least one of real-time calorie consumption efficiency and a workout limit. The acceleration and/or user's motion measured by the acceleration sensor 115B and/or the motion tracking sensor 115F may be used to determine at least one of the real-time calorie consumption efficiency and the quality of a postural exercise. The sensor module 115 may further include a respiration sensor. For example, the respiration rate measured by the respiration sensor may be used to determine the quality of a postural exercise.

At operation 420, the electronic device 120 may acquire user's body data, based on the received user's first biometric signal.

According to various embodiments, the processor of the electronic device 120 may acquire user's body data by comprehensively analyzing various kinds of biometric information such as a body index, a health status, etc., based on the received user's first biometric signal. For example, based on the user's first biometric signal, the user's body data about at least one of body part size, heart rate, respiratory rate, body fat percentage, stress index, posture, muscle strength, walking speed, and body weight may be acquired.

At operation 430, the electronic device 120 may receive an input for establishing a goal. If there is a pre-established goal, or if it is configured to automatically establish a goal according to the acquired user's body data, the operation 430 may be omitted.

The input for establishing a goal may be at least one of, for example, a target weight, a target body shape, a desired calorie consumption amount, a desired workout period, a target energy consumption amount, a fitness content target, and a right target posture.

At operation 440, the electronic device 120 may calculate a required workout amount, based on the acquired body data and the established goal. For example, when an input for setting a target weight is received, the electronic device 120 may calculate the required workout amount by comprehensively analyzing a current weight, a target weight, the date of reaching the target weight, a daily calorie intake amount, and a daily calorie burning rate. The required workout amount may include at least one of a required calorie consumption amount, a workout period, and fitness content information.

According to various embodiments, metadata may be used to calculate the required workout amount. The metadata may be used when the calorie consumption, the body index change, or the like is not sufficiently measured while the user of the wearable device 110 performs workout. The metadata may include, for example, the caloric consumption, the body index change, or the like that is obtained by normally analyzing the correlation between the body index and the fitness content. For example, if the body indexes of the user of the wearable device 110 are 175 cm in height, 80 kg in weight, male in sex, and 30 years old, the electronic device 120 may refer to the metadata that when a 30-year-old man with a height of 175 cm and a weight of 80 kg consumes 1000 calories when performing fitness content A for one hour. Then, the electronic device 120 may calculate the required workout amount, based on the metadata. The metadata according to the correlation between the body index and the fitness content is widely known to those skilled in the art through various academic materials and commercialized algorithms, and a detailed description thereof will be omitted.

According to various embodiments, accumulated user record data and/or big data may be used to calculate the required workout amount. When there is a record in which the user wears the wearable device 110 and performs workout, the electronic device 120 may store a workout record as record data. The electronic device 120 may analyze the correlation between the body data and the fitness content through the accumulated user record data, and also calculate the required workout amount by personalizing/customizing the calorie consumption amount, etc. resulting from performing the fitness content. If the user record data is accumulated over a certain level, it may be converted into big data.

According to various embodiments, the electronic device 120 may store distinctively user's body data associated with first and second biometric signals. For example, the first biometric signal may include long-term altered body data. The long-term altered body data may include, for example, at least one of body size, body fat, and muscle size. On the other hand, the second biometric signal may include body data that varies in real time by workout. The body data varying in real time may include, for example, at least one of motion, heart rate, workout amount, and workout quality. The electronic device 120 may separately store, as user record data, the body data associated with the first and second biometric signals.

At operation 450, the electronic device 120 may monitor a user's workout state. According to various embodiments, the electronic device 120 may detect a change in motions and biometric signals of the user wearing the wearable device 110, and determine whether the user is in a state of workout. If it is determined that the user wearing the wearable device 110 is in a state of workout, the electronic device 120 may receive the user's second biometric signal and collect changes in body data and the like. For example, changes in EMG, respiration, heart rate, electrocardiogram, and acceleration of the user wearing the wearable device 110 may be collected.

According to a certain embodiment, the electronic device 120 may collect changes in the user's body data, etc. and provide personalized exercise guide. For example, after checking whether a right muscle is used, whether breathing is proper, whether a suitable heart rate is maintained, whether a workout posture is proper, and the like, the personalized exercise guide may be provided. A detailed description will be given later with reference to FIG. 10.

At operation 460, the electronic device 120 may compare and analyze a change of the user's body data estimated based on the calculated required amount of workout and an actual change of the user's body data resulting from workout.

According to various embodiments, the electronic device 120 may store accumulatively user's workout records and/or body data changes. The electronic device 120 may analyze the correlation between the workout amount and the body data change by referring to the stored user's workout records and body data changes. The electronic device 120 may estimate a user's body data change according to the workout amount, based on the analyzed correlation. For example, if the user performs workout according to the calculated required workout amount, the electronic device 120 may estimate a change in the user's body data.

The electronic device 120 may compare and analyze an actual change of the user's body data resulting from workout and the estimated change of the user's body data.

At operation 470, the electronic device 120 may correct the calculated required workout amount when it is determined that a result of comparing and analyzing the estimated body data change and the actual body data change is out of a predetermined error range. For example, even when the same user performs the same workout, the change of the body data may be varied according to various factors. The electronic device may previously store the error range of the estimated body data change based on the required workout amount. When it is determined that a result of comparing and analyzing the estimated body data change and the actual body data change is out of a predetermined error range, the electronic device 120 may reflect this on the accumulated record data and/or big data. The calculated required amount of workout may be corrected using the reflected record data and/or big data. Correcting the required workout amount allows providing a more personalized required workout amount to the user. If it is determined that a result of comparing and analyzing the estimated body data change and the actual body data change is within a predetermined error range, the electronic device 120 may maintain the calculated required workout amount without correction.

Figure 5:
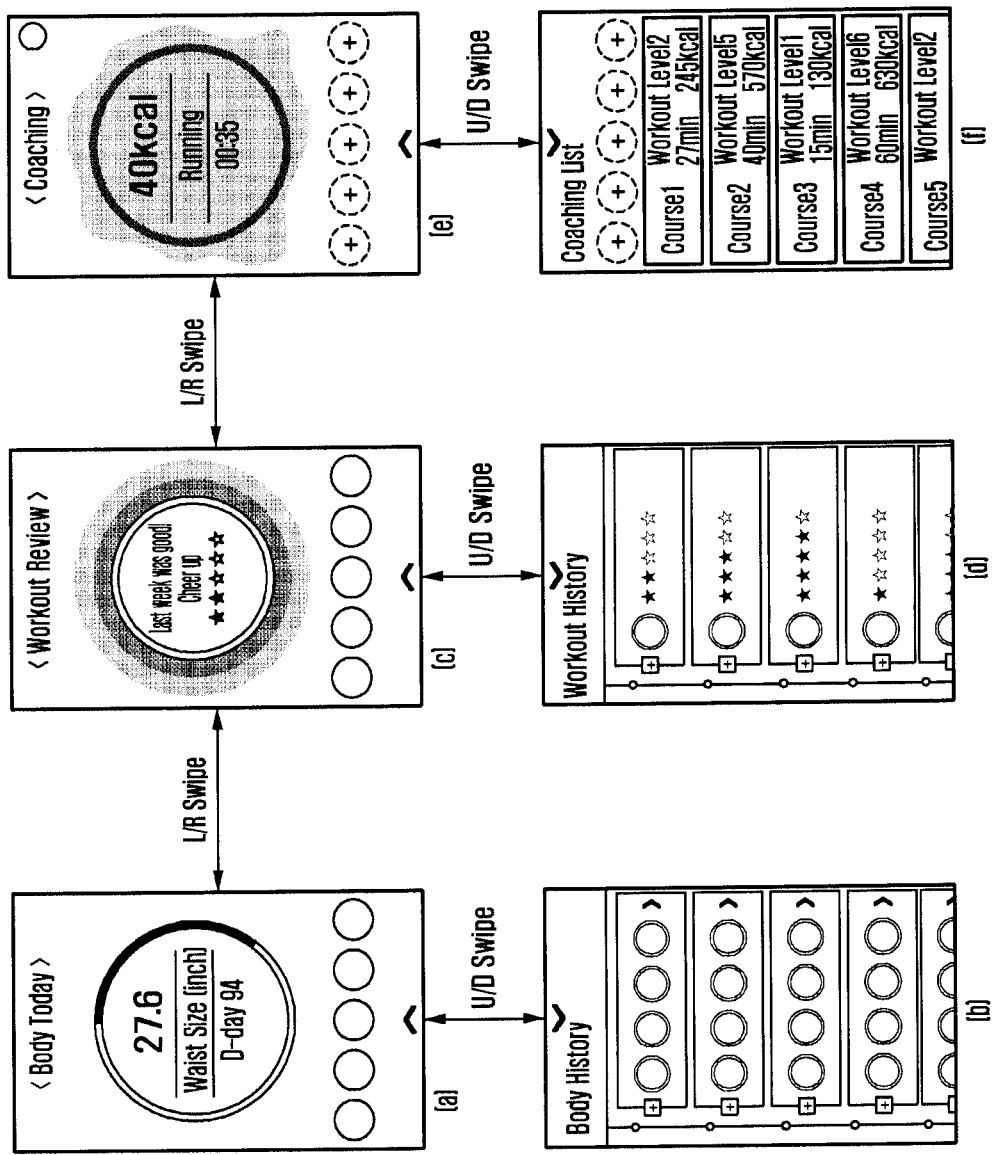
FIG. 5 schematically shows a user interface of a personalized exercise guide according to various embodiments.

FIG. 5 schematically shows a user interface of a personalized exercise guide according to various embodiments.

Referring to FIG. 5, (a) of FIG. 5 shows a user interface indicating the body data and change record measured based on the received first biometric signal. When an input for swiping downward a user interface screen of FIG. 5 (*a*) is received from the user, the electronic device may display a user's body data history page on the screen with a user interface as shown in (b) of FIG. 5. Also, when an input for swiping rightward the user interface screen of FIG. 5 (*a*) is received from the user, the electronic device may display a screen for showing the measured workout activity and/or the collected record on a user interface as shown in (c) of FIG. 5. When an input for swiping downward the user interface screen of FIG. 5 (*c*) is received from the user, the electronic device may display a workout record history page on the screen with a user interface as shown in (d) of FIG. 5. When an input for swiping rightward the user interface screen of FIG. 5 (*c*) is received, the electronic device may display a personalized exercise guide on the screen with a user interface as shown in (e) of FIG. 5. When an input for swiping downward the user interface screen of FIG. 5 (*e*) is received, the electronic device may display a user interface for selecting a course of exercise on the screen as shown in (f) of FIG. 5. A detailed description of each user interface will be described later.

Figure 6A:
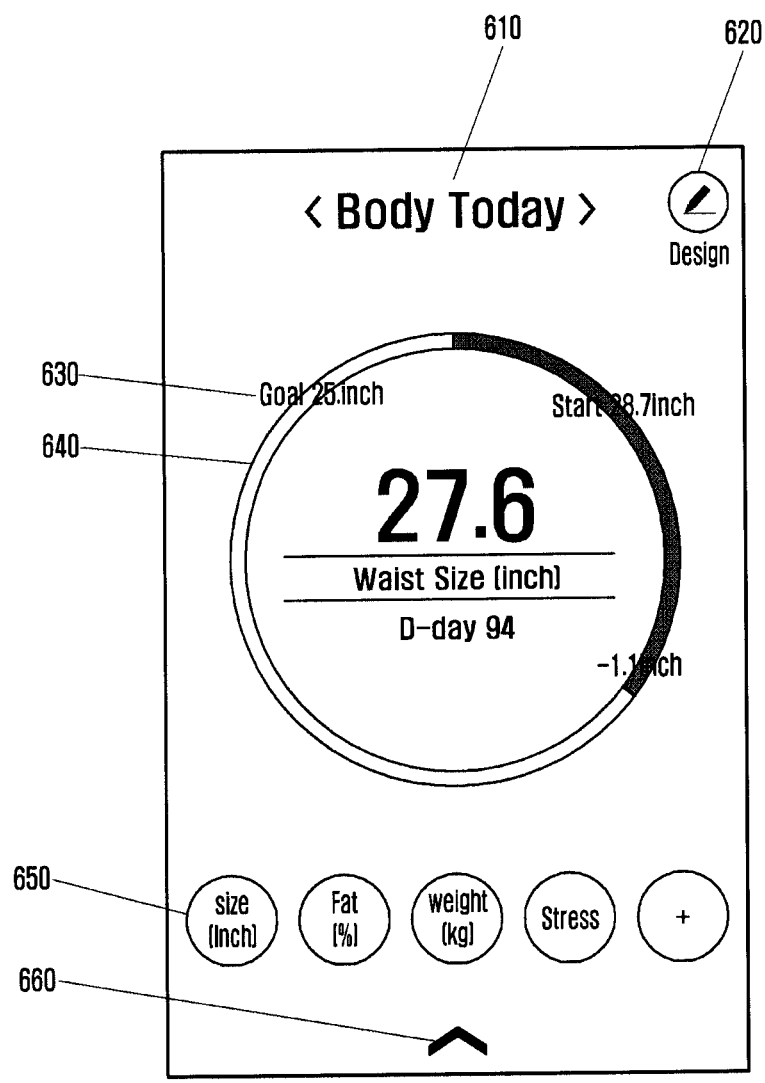
Figure 7:
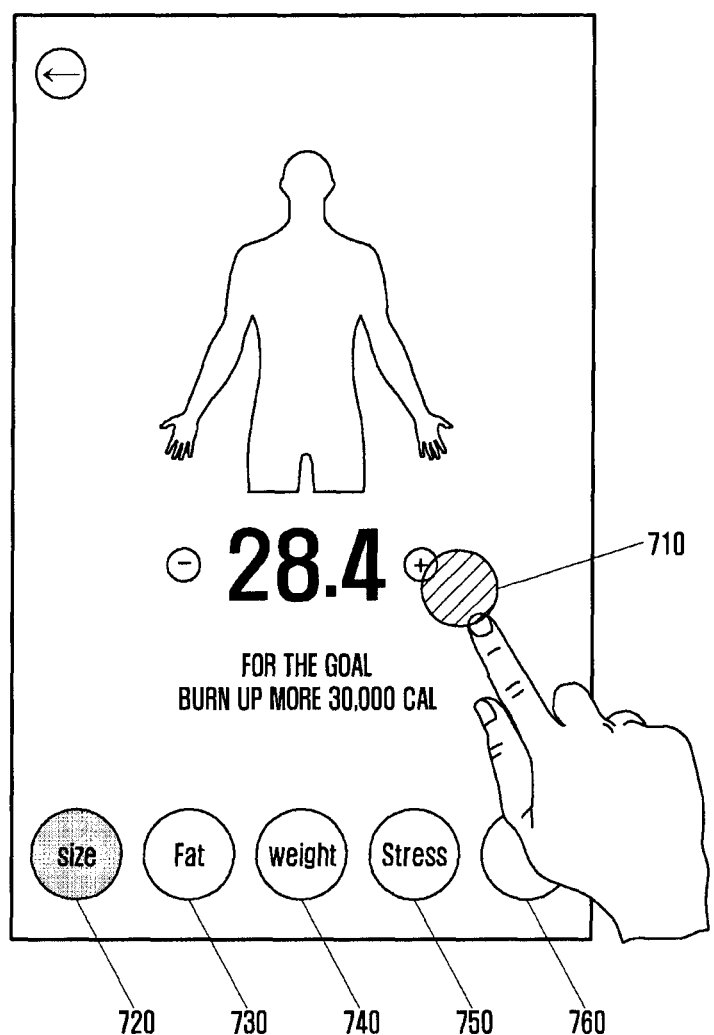

FIGS. 6A to 7 are exemplary diagrams showing a user interface allowing a user to establish a goal in an embodiment.

Referring to FIG. 6A, the user interface may include a service page switch key 610, a design page switch key 620, a progress state information indicator 630, a current state indicator 640, a body data page switch key 650, and a history page switch key 660. For example, the service page switch key 610 allows switching from a current service page to a guide service page, and vice versa. The design page switch key 620 allows switching to a design page that allows the user to directly set a target body size, a target body fat, a target weight, and the like. The progress state information indicator 630 allows the user to intuitively perceive initially acquired body data, current body data, and target body data (e.g., body size, body fat, body weight, etc.). The current state indicator 640 allows the user to intuitively perceive user data (e.g., body size, body fat, body weight, stress information, date information for achieving goal, etc.) acquired based on the first biometric signal. The body data page switch key 650 allows switching to a page that provides more detailed information about, for example, body size, body fat, weight, stress information, and the like. The history page switch key 660 allows switching to a history page that provides, for example, body size, body fat, weight, and stress information.

When the design page switch key 620 of FIG. 6A is selected, a design page appears as shown in FIG. 6B. Referring to FIG. 6B, (a) of FIG. 6B shows an embodiment of setting a target waist size, (b) of FIG. 6B shows an embodiment of setting a target weight, and (c) of FIG. 6B shows an embodiment of setting a target body fat. Through this user interface, the user may intuitively establish a goal. For example, to establish a desired goal, the user may touch or drag a wheel 670 displayed on a ring-shaped user interface for setting the target body fat.

FIG. 7 shows a user interface of a design page according to another embodiment.

Referring to FIG. 7, the user may set a desired target body size by touching 710 a button displayed on an interface for setting a body size. Also, the user interface may be displayed to allow the user to intuitively perceive a change of a body shape according to the set target body size. The user interface may allow size setting 720, body fat setting 730, weight setting 740, and stress setting 750.

Figure 8:
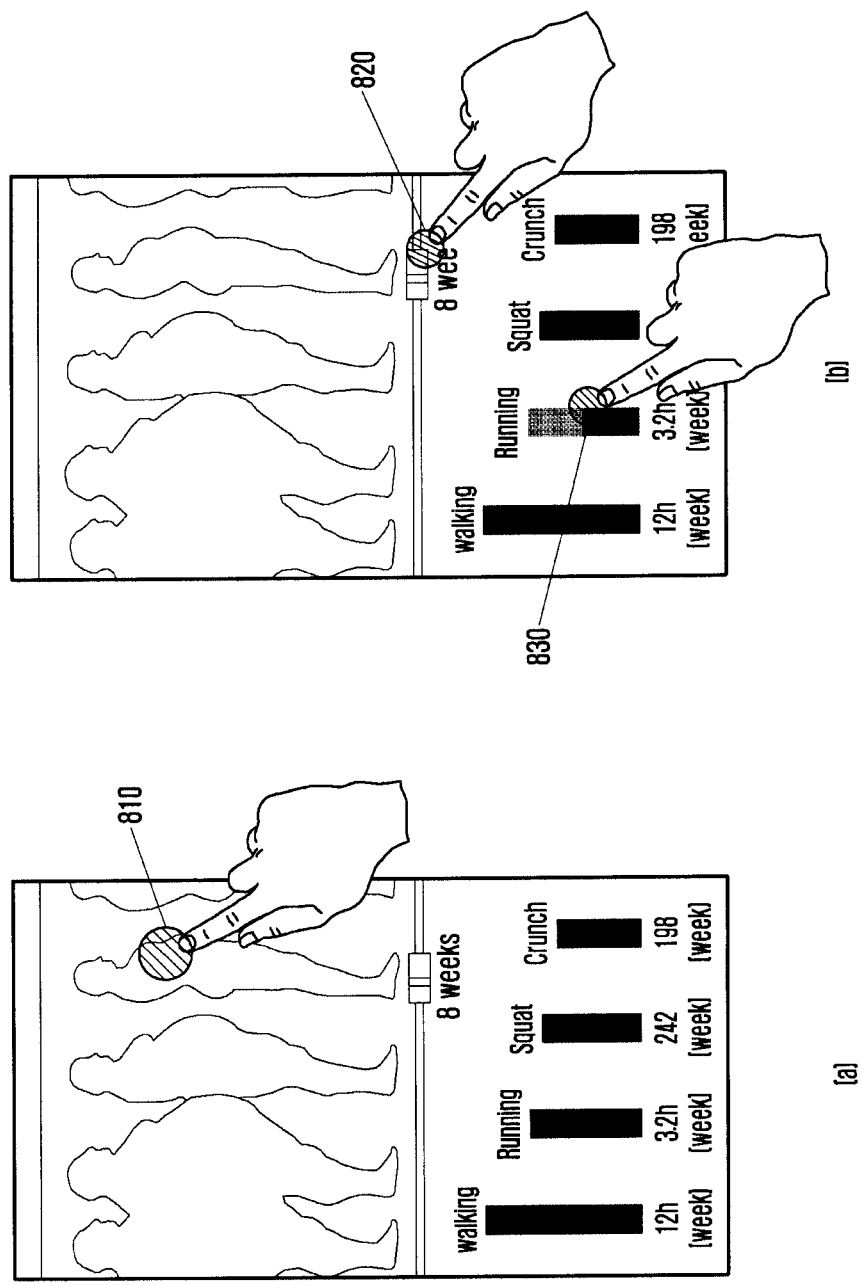
FIG. 8 shows a user interface of displaying a required workout amount in accordance with an established goal in an embodiment.

FIG. 8 shows a user interface of displaying a required workout amount in accordance with an established goal in an embodiment.

Referring to FIG. 8 (*a*), the user can set a desired body shape and/or a desired workout period. For example, the user may set a desired body shape by touching 810 the desired body shape displayed on the body shape setting interface. The electronic device 120 may calculate the required workout amount, based on the user's body data and the body shape desired by the user, and then may display the calculated amount on a user interface. For example, 12 hours of walking, 3.2 hours of running, 242 squats, and 198 crunches may be calculated as required weekly fitness contents and displayed with a user interface.

Figure 9:
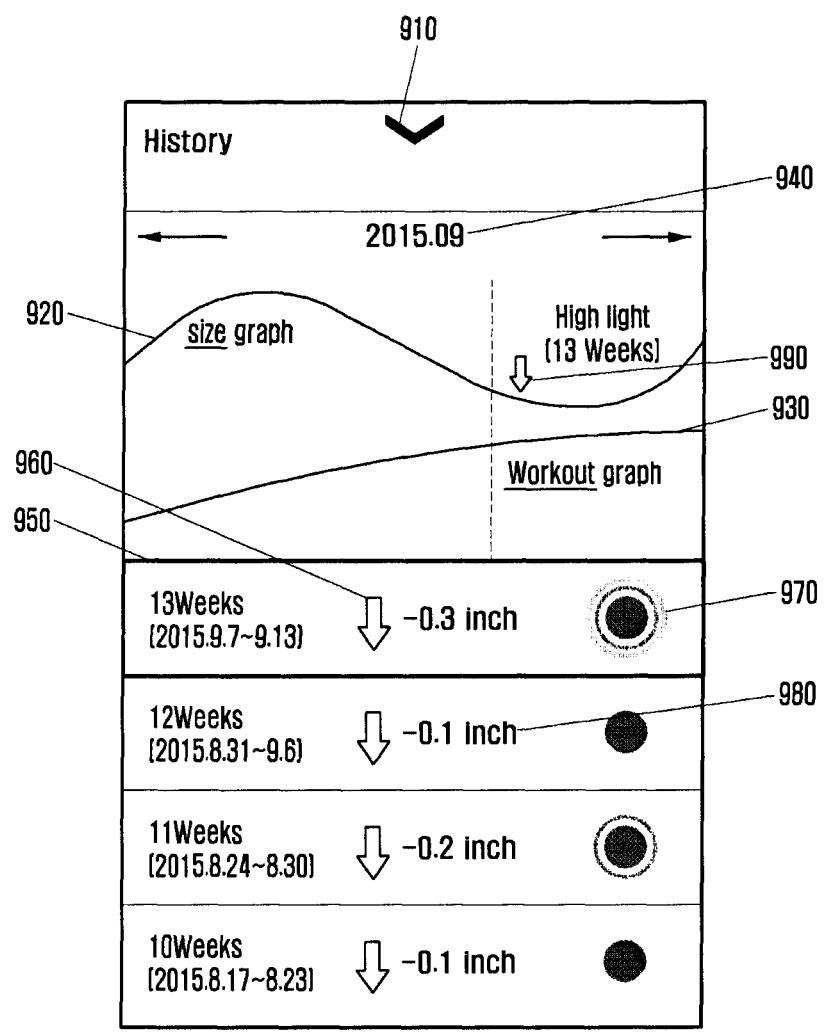
FIG. 9 shows a history page displayed in response to selection of a history page switch key of FIG. 6A in an embodiment.

Referring to FIG. 8 (*b*), the user may adjust the required workout amount displayed on the user interface. For example, a workout period 820 or a running time 830 may be adjusted. Although not shown, the fitness contents may be changed. [92] FIG. 9 shows a history page displayed in response to selection of a history page switch key of FIG. 6A in an embodiment. [93] Referring to FIG. 9, the user may switch a page by selecting a page switch key 910 displayed on a user interface. A body data graph 920 may be generated and displayed at regular intervals of time. The body data may be, for example, body size, body fat, body weight, and stress index. In FIG. 9, the body size data is generated and displayed monthly as a trend graph. A workout activity graph 930 may be a graph generated and displayed for a workout activity. A swipe key 940 allows the user to directly swipe a graph area to view desired body data (e.g., size, body fat, weight, stress variation values, exercise scores, etc.) around a reference point. The weekly data 950 may represent a change of weekly body data based on accumulated record data. In the weekly data, a specific week having the greatest change of the body data may be highlighted, for example, displayed with a crown icon. In FIG. 9, a highlight 990 is displayed on the graph. The weekly data 950 may include a fluctuation indicator 960 and infography 970. The fluctuation indicator may provide fluctuations about body size, body fat, weight, or stress. The infography 970 may provide a weekly workout score (e.g., workout effect and workout quality). The user may touch a specific week in the weekly data 950 to see detailed information of the selected week.

Figure 10:
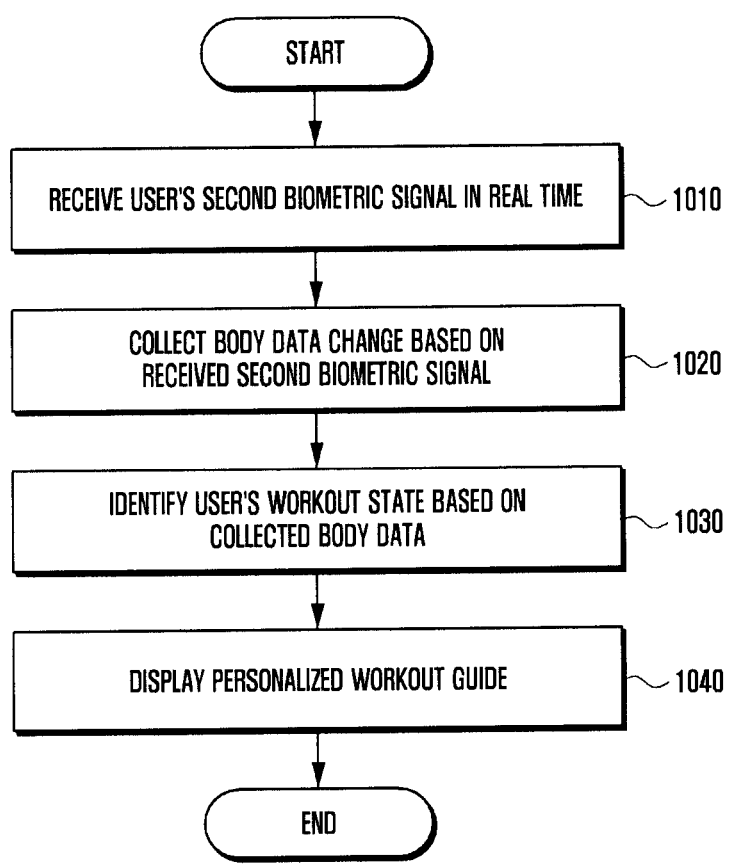
FIG. 10 is a flow diagram illustrating a method for monitoring a workout state and displaying a personalized exercise guide according to various embodiments.

FIG. 10 is a flow diagram illustrating a method for monitoring a workout state and displaying a personalized exercise guide according to various embodiments.

Referring to FIG. 10, at operation 1010, the electronic device 120 may receive a user's second biometric signal measured by the sensor.

According to various embodiments, the electronic device 120 may control the wearable device 110 to measure the second biometric signal of a user who wears the wearable device 110. For example, when an input for measuring the user's second biometric signal is received, the electronic device 120 may transmit a command to measure the user's second biometric signal to the wearable device 110 via the communication module 122. The wearable device 110 that receives the command may control the sensor module 115 to measure the second biometric signal of the user wearing the wearable device 110. When the user's second biometric signal is measured, the wearable device 110 may transmit the measured second biometric signal to the electronic device 120 via the communication interface 112. Then, the electronic device 120 may receive the user's second biometric signal through the communication module 122.

According to various embodiments, the second biometric signal may include a change in biometric information caused by a user's motion. The electronic device 120 may detect changes in motion and biometric signal of the user who wears the wearable device 110, and may determine whether the user is in a workout state. If it is determined that the user wearing the wearable device 110 is in a state of workout, the electronic device 120 may control the wearable device 110 to measure the user's second biometric signal in real time. According to a certain embodiment, the electronic device 120 may receive a signal indicating a user's workout state and control the wearable device 110 to measure the user's second biometric signal in real time.

At operation 1020, the electronic device 120 may collect changes in the user's body data based on the received second bio-signal.

According to various embodiments, the electronic device 120 may collect changes in body data of the user wearing the wearable device 110. For example, it is possible to collect at least one of changes in EMG, breathing, heart rate, ECG pattern, and acceleration. The collected EMG change may be a change in muscle use of each body part of the user who wears the wearable device 110. The collected breathing change may be a change in breathing (e.g., inhalation, exhalation, pattern, etc.) of the user who wears the wearable device 110. The collected heart rate change may be a change in heart rate per minute. The collected ECG pattern change may be a change in potentials (e.g., regular or irregular pattern, etc.) related to the heart rate of the user who wears the wearable device 110. The collected acceleration change may be a change in posture, balance, and motions of the user who wears the wearable device 110.

At operation 1030, the electronic device 120 may identify a user's workout state, based on the collected changes in body data.

According to various embodiments, the electronic device 120 may check a workout state of the user wearing the wearable device 110, based on the collected changes of the user's body data. For example, it is possible to check, from the collected EMG changes, whether the user wearing the wearable device 110 is using muscles accurately and correctly according to the fitness contents being performed. Also, it is possible to check, from the collected breathing changes, whether the user wearing the wearable device 110 is breathing properly according to the fitness contents being performed. Also, it is possible to check, from the collected ECG patterns, whether the user wearing the wearable device 110 is performing an excessive workout. Also, it is possible to check, from the collected acceleration change, whether the user wearing the wearable device 110 is performing a workout in a correct posture according to the fitness contents being performed.

At operation 1040, the electronic device 120 may display a personalized workout guide, based on the identified workout state of the user.

According to various embodiments, the electronic device 120 may control the display to display a personalized workout guide, based on the identified workout state of the user wearing the wearable device 110. For example, the efficiency of aerobic exercise, the quality of anaerobic exercise, whether a risk situation is recognized, etc. may be visually displayed on the display so that the user of the electronic device 120 can intuitively perceive it.

According to various embodiments, the electronic device 120 may recommend a suitable workout, based on the received first and second biometric signals of the user. For example, the first biometric signal may include long-term altered body data. The long-term altered body data may include, for example, at least one of body size, body fat, and muscle size. On the other hand, the second biometric signal may include body data that varies in real time by workout. The body data varying in real time may include, for example, at least one of motion, heart rate, workout amount, and workout quality. Based on the received first and second biometric signals of the user, the electronic device 120 may identify and recommend a suitable workout for the user.

According to various embodiments, the electronic device 120 may provide a user interface to allow the user to directly select a workout type and/or a workout course.

Figure 11:
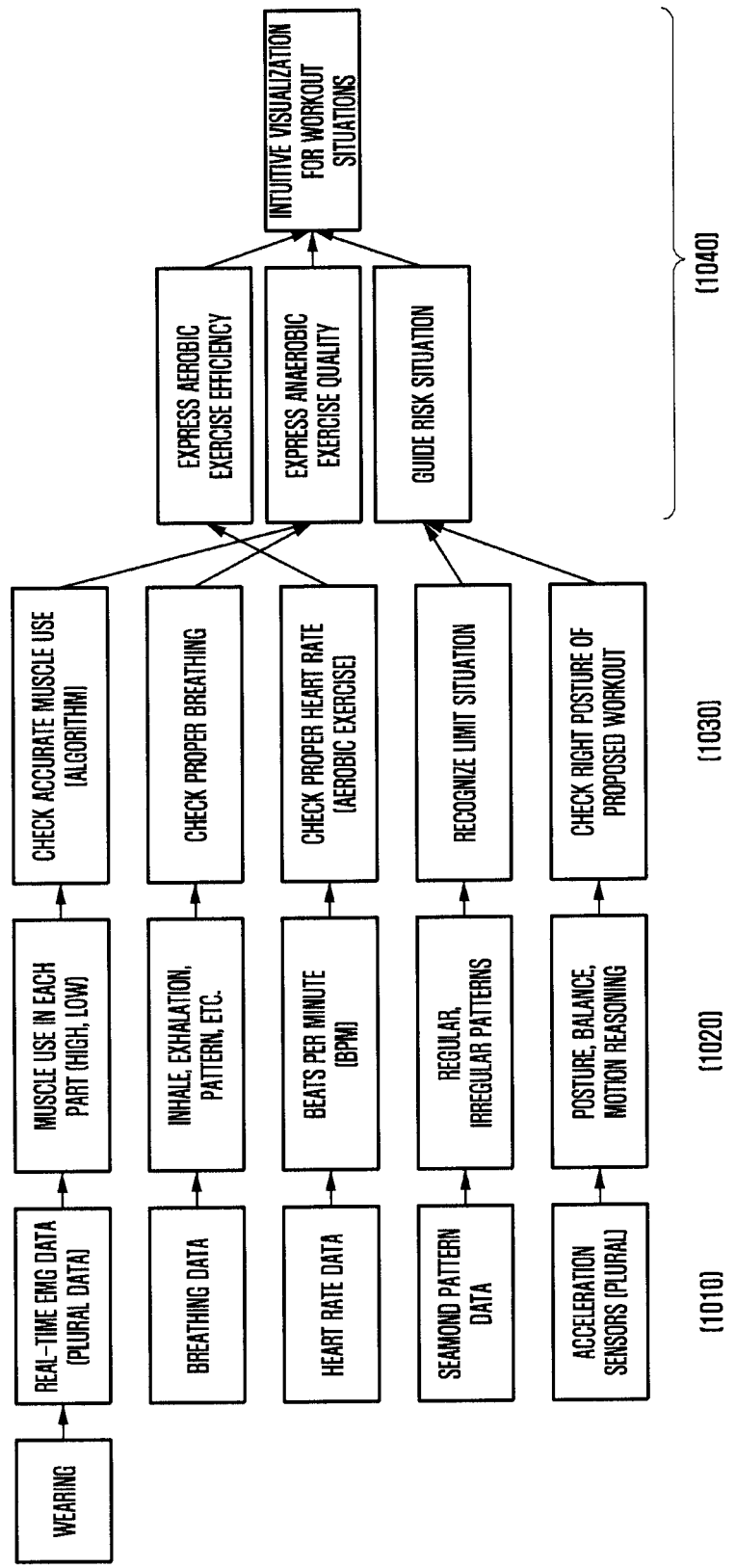
FIG. 11 illustrates a process for monitoring a workout state and displaying a personalized exercise guide according to an embodiment of FIG. 10.

FIG. 11 illustrates a process for monitoring a workout state and displaying a personalized exercise guide according to an embodiment of FIG. 10. For example, when real-time EMG data is measured, it is possible to collect changes in muscle use in each body part and check whether accurate muscle is being used. When breathing data is measured, it is possible to collect inhalation, expiration, and pattern, and check whether proper breathing is made. When heart rate data is measured, it is possible to collect heartbeats per minute and check whether a proper heart rate is effectively maintained (e.g., during aerobic exercise). When ECG pattern data is measured, it is possible to collect regular or irregular patterns, and check whether this is a limit situation. When acceleration information is measured, it is possible to collect posture, balance, and motion, and check whether a right posture is maintained according to the proposed workout.

The checked information may be visualized as at least one of the efficiency of aerobic exercise, the quality of anaerobic exercise, and the risk situation guide, and also displayed on the display.

Figure 12:
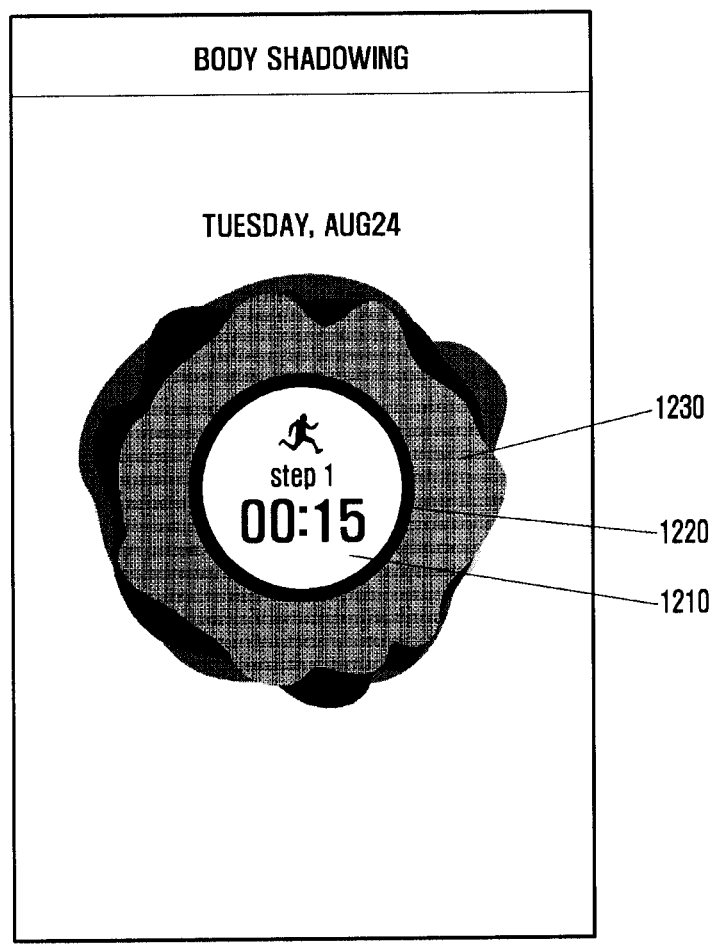
FIG. 12 shows a user interface of a personalized exercise guide according to an embodiment.

FIG. 12 shows a user interface of a personalized exercise guide according to an embodiment.

Referring to FIG. 12, an information indicator 1210 may indicate fitness content, posture, strength, number of times, time, and the like. For example, FIG. 12 shows that the information indicator 1210 indicates that the first step of running is performed for 15 seconds. A circular graph 1220 may represent a daily progress or the progress of a current fitness program. A guide indicator 1230 may visualize and display the efficiency of aerobic exercise, the quality of anaerobic exercise, the presence or absence of a risk situation, etc. so that the user of the electronic device 120 can intuitively perceive. For example, the heart rate per minute may be visualized and displayed through real-time variations in synchronized wave or area. In a certain embodiment, the calorie consumption, exercise quality, exercise intensity, or quality of posture exercise may be visualized and displayed through real-time variations in area. In another embodiment, the quality of posture exercise, moving strength, moving speed, or EMG intensity may be visualized and displayed through variations in color. In still another embodiment, the presence of risk situation or body limitation may be visualized and displayed through color.

Figure 13:
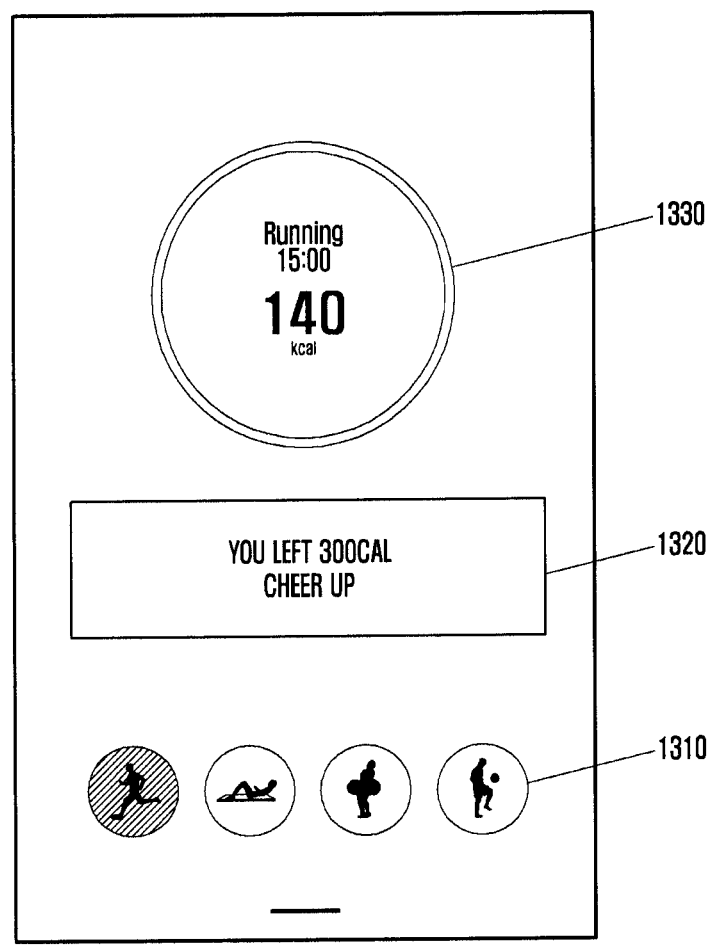
FIG. 13 shows a user interface of a personalized exercise guide according to an embodiment.

FIG. 13 shows a user interface of a personalized exercise guide according to an embodiment.

Referring to FIG. 13, a progress bar 1310 may represent the order and progress of today's workout courses. A coaching board 1320 may represent a message associated with the degree of achievement and a real-time guide message. An information indicator 1330 may represent a current workout state (including speed), a predetermined time/number of times, calorie efficiency (fat burning), a completion level of motion, and the like.

According to various embodiments, the personalized exercise guides may be classified into a free mode and a program mode depending on whether there is an exercise course or a predetermined progress order.

In the free mode, the progress bar 1310 may be omitted, and the coaching board 1320 may provide the remaining calorie consumption and a message associated with target achievement in real time. In addition, the information indicator 1330 may provide at least one of calorie consumption efficiency (e.g., 1 to 6 levels), real-time progress time and frequency, current workout type, and speed information in case of walking or running.

In the program mode, the progress bar 1310 may represent a workout sequence and progress (e.g., up to 5 workouts). The coaching board 1320 may provide feedback for at least one of breathing, speed, and balance posture. In addition, the coaching board 1320 may provide a reference for achieving a programmed workout. The information indicator 1330 may represent the quality of posture and workout and may provide additional comments. In addition, the information indicator 1330 may provide at least one of a predetermined time and frequency, a current workout type among the exercise courses, and speed information in case of walking/running.

Figure 14:
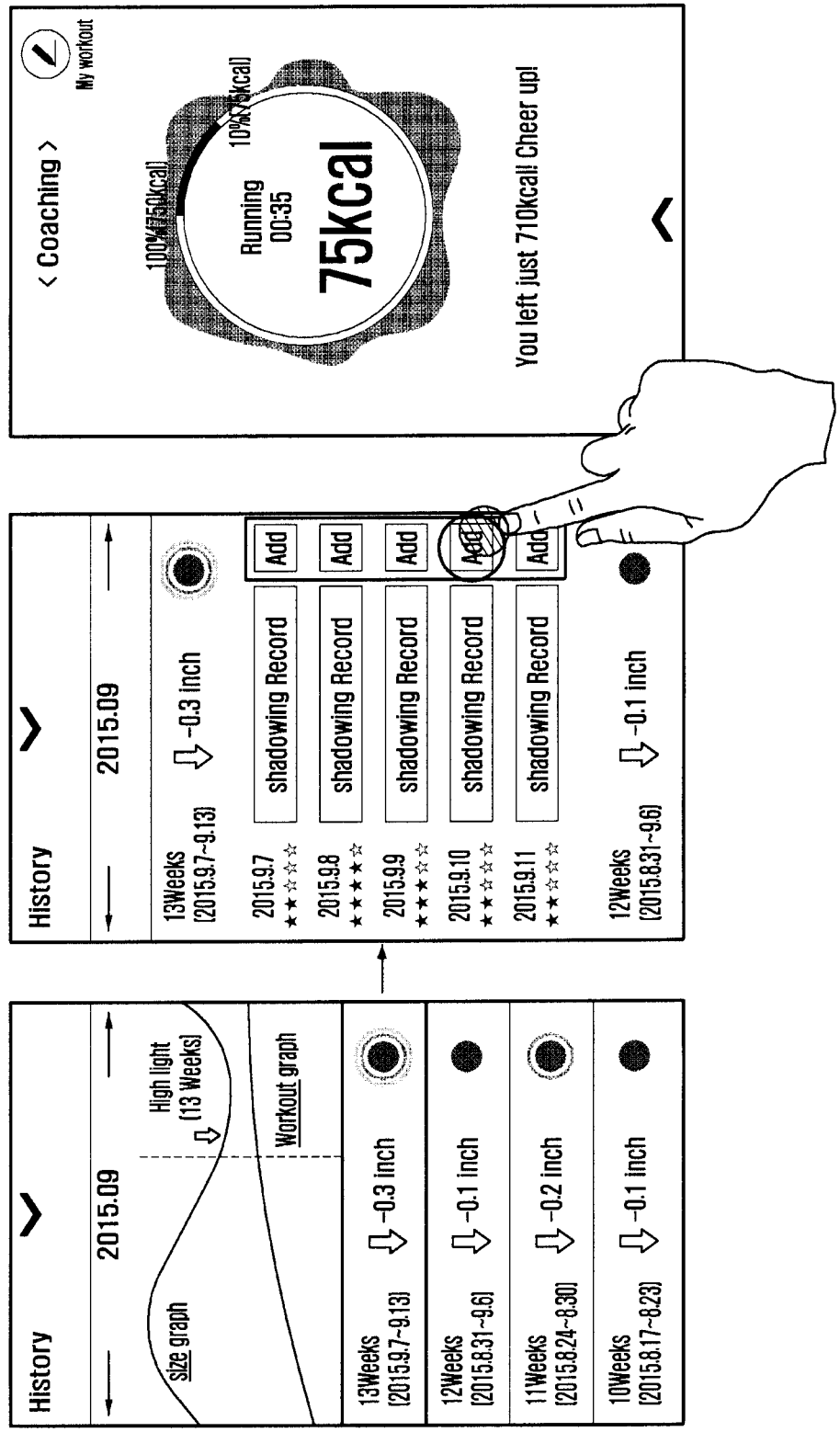
FIG. 14 shows a user interface for selecting a course of exercise according to an embodiment.

FIG. 14 shows a user interface for selecting a course of exercise according to an embodiment.

Referring to FIG. 14, (a) of FIG. 14 shows a history page shown in FIG. 9. For example, the user may touch 13th week in the page shown in FIG. 14. The electronic device 120 recognizes this touch as a command to jump to a page of detailed information about the 13th week and thereby switch the current page to the 13th week information page. For example, (b) of FIG. 14 shows detailed information of the 13th week. The detailed information page of the selected week may be visualized and displayed intuitively, including daily workout records and daily workout performance. A shadowing record shown in FIG. 14 (b) may include information such as an exercise course and/or an activity record. The user may check the daily workout record and add the exercise course of a specific day to a current coaching interface. For example, a user who wishes to use the same exercise course as that of Sep. 10, 2015 in FIG. 14 (b) may check the shadowing record of Sep. 10, 2015 and add the exercise course of Sep. 10, 2015 to the coaching interface. Then the added exercise course of Sep. 10, 2015 may be displayed on the personalized exercise guide user interface.

According to various embodiments of the present invention, a method for providing a personalized exercise guide at an electronic device may comprise receiving a user's first biometric signal measured by at least one sensor; acquiring user's body data, based on the received first biometric signal; calculating a required amount of workout, based on the acquired body data and a pre-established goal; and comparing and analyzing a body data change estimated based on the calculated required amount of workout and an actual body data change resulting from workout.

According to various embodiments of the present invention, the at least one sensor may be included in another electronic device.

According to various embodiments of the present invention, the user's body data may include at least one of body part size, heart rate, respiratory rate, body fat percentage, stress index, posture, muscle strength, walking speed, and body weight.

According to various embodiments of the present invention, the method may further comprise receiving an input for establishing a goal.

According to various embodiments of the present invention, the method may further comprise determining whether a result of comparing and analyzing the estimated body data change and the actual body data change is out of a predetermined error range; and correcting the calculated required amount of workout when the result is out of the predetermined error range.

According to various embodiment of the present invention, the method may further comprise monitoring a user's workout state.

According to various embodiment of the present invention, the method may further comprise detecting a change in motions and biometric signals of the user; and determining whether the user is in a state of workout, based on the detected change in motions and biometric signals.

According to various embodiments of the present invention, the method may further comprise receiving a user's second biometric signal measured by the at least one sensor; collecting a change in user's body data, based on the received second biometric signal; identifying a user's workout state, based on the collected change in body data; and displaying a personalized exercise guide, based on the identified user's workout state.

According to various embodiments of the present invention, the personalized exercise guide may include an efficiency of aerobic exercise, a quality of anaerobic exercise, information about whether a risk situation is recognized, and a combination thereof.

According to various embodiments of the present invention, the user's body data may be stored distinctively according to the received first and second biometric signals.

According to various embodiments of the present invention, the displaying a personalized exercise guide may include displaying a recommended workout analyzed based on the received first and second biometric signals.

While the present disclosure has been particularly shown and described with reference to exemplary embodiments thereof, it is clearly understood that the same is by way of illustration and example only and is not to be taken in conjunction with the present disclosure. It will be understood by those skilled in the art that various changes in form and details may be made therein without departing from the subject matter and scope of the present disclosure.

The invention claimed is:

1. A method for providing a personalized exercise guide at an electronic device, the method comprising:
   electronically receiving a user's first biometric signal transmitted by a first sensor;
   acquiring the user's body data, based on the received first biometric signal;
   calculating a required amount of workout, based on the acquired user's body data and a pre-established goal;

comparing and analyzing a body data change estimated based on the calculated required amount of workout and an actual body data change resulting from workout;
determining whether a result of comparing and analyzing the estimated body data change and the actual body data change is out of a predetermined error range;
correcting the calculated required amount of workout when the result is out of the predetermined error range;
providing the personalized exercise guide based on the body data change and the corrected required amount of workout;
displaying a user's body data history, a measured workout activity, a workout record history, the personalized exercise guide, and a user interface for selecting a course of exercise, using a plurality of pages; and
displaying whether a risk situation is recognized based on the received first biometric signal,
wherein the personalized exercise guide includes a workout type and a workout course recommended for the user.

2. The method of claim 1, wherein the first sensor is included in another electronic device.

3. The method of claim 1, wherein the user's body data includes at least one of body part size, heart rate, respiratory rate, body fat percentage, stress index, posture, muscle strength, walking speed, and body weight.

4. The method of claim 1, further comprising:
electronically receiving the user's second biometric signal transmitted by second sensor;
collecting a change in the user's body data, based on the received second biometric signal;
identifying the user's workout state, based on the collected change in body data; and
displaying the personalized exercise guide,
wherein the personalized exercise guide is determined further based on the identified user's workout state.

5. The method of claim 1, further comprising:
receiving the user's second biometric signal measured by a second sensor;
collecting a change in the user's body data, based on the received second biometric signal;
identifying the user's workout state, based on the collected change in body data; and
displaying the personalized exercise guide,
wherein the personalized exercise guide further includes at least one of an efficiency of aerobic exercise, or a quality of anaerobic exercise.

6. The method of claim 4, wherein the user's body data is stored distinctively according to the received first and second biometric signals.

7. The method of claim 4, wherein the displaying the personalized exercise guide includes displaying a recommended workout analyzed based on the received first and second biometric signals.

8. An electronic device comprising:
a communication module electronically receiving a user's first biometric signal transmitted by a first sensor included in another electronic device;
a display displaying body data and a required amount of workout;
a memory storing instructions; and
a processor electronically connected to the communication module, the display, and the memory,
wherein the instructions stored in the memory cause, upon execution, the processor to acquire the user's body data, based on the received first biometric signal, to calculate the required amount of workout, based on the acquired user's body data and a pre-established goal, to compare and analyze a body data change estimated based on the calculated required amount of workout and an actual body data change resulting from workout, to determine whether a result of comparing and analyzing the estimated body data change and the actual body data change is out of a predetermined error range, to correct the calculated required amount of workout when the result is out of the predetermined error range, to provide a personalized exercise guide based on the body data change and the corrected required amount of workout, to display the user' body data history, a measured workout activity, a workout record history, the personalized exercise guide, and a user interface for selecting a course of exercise, using a plurality of pages, and to display whether a risk situation is recognized based on the received first biometric signal, wherein the personalized exercise guide includes a workout type and a workout course recommended for the user.

9. The electronic device of claim 8, wherein the another electronic device is a fabric-type or cloth-type wearable device.

10. The electronic device of claim 8, further comprising:
an input device receiving an input for establishing a goal.

11. The electronic device of claim 8, wherein the instructions further cause the processor to receive the user's second biometric signal measured by a second sensor, to collect a change in the user's body data, based on the received second biometric signal, to identify the user's workout state, based on the collected change in body data, and to display the personalized exercise guide, wherein the personalized exercise guide is determined further based on the identified user's workout state.

12. The electronic device of claim 11, wherein the instructions further cause the processor to display a recommended workout analyzed based on the received first and second biometric signals.

13. A system for providing a personalized exercise guide, the system comprising:
a wearable device measuring a user's first biometric signal through first sensor, and transmitting the measured first biometric signal to an electronic device; and
the electronic device receiving the measured first biometric signal from the wearable device, acquiring the user's body data, based on the received first biometric signal, calculating a required amount of workout, based on the acquired user's body data and a pre-established goal, comparing and analyzing a body data change estimated based on the calculated required amount of workout and an actual body data change resulting from workout, determining whether a result of comparing and analyzing the estimated body data change and the actual body data change is out of a predetermined error range, correcting the calculated required amount of workout when the result is out of the predetermined error range, providing the personalized exercise guide based on the body data change and the corrected required amount of workout, displaying the user' body data history, a measured workout activity, a workout record history, the personalized exercise guide, and a user interface for selecting a course of exercise, using a plurality of pages, and displaying whether a risk situation is recognized based on the received first biometric signal, wherein the personalized exercise guide includes a workout type and a workout course recommended for the user.

\* \* \* \* \*